United States Patent
Kim et al.

(10) Patent No.: US 9,999,676 B2
(45) Date of Patent: Jun. 19, 2018

(54) BIODEGRADABLE MICROBEAD COMPRISING ANIONIC POLYMER FOR IMPROVING ADSORPTIVE POWER TO ANTICANCER DRUGS, AND METHOD FOR PREPARING SAME

(71) Applicant: UTAH-INHA DDS & ADVANCED THERAPEUTICS RESEARCH CENTER, Incheon (KR)

(72) Inventors: Se Yoon Kim, Gyeonggi-do (KR); Don Haeng Lee, Seoul (KR); Yixian Li, Incheon (KR)

(73) Assignee: UTAH-INHA DDS & ADVANCED THERAPEUTICS RESEARCH CENTER, Incheon (KR)

( * ) Notice: Subject to any disclaimer, the term of this patent is extended or adjusted under 35 U.S.C. 154(b) by 0 days. days.

(21) Appl. No.: 14/647,270

(22) PCT Filed: Nov. 15, 2013

(86) PCT No.: PCT/KR2013/010420
§ 371 (c)(1),
(2) Date: May 26, 2015

(87) PCT Pub. No.: WO2014/084530
PCT Pub. Date: Jun. 5, 2014

(65) Prior Publication Data
US 2015/0297732 A1  Oct. 22, 2015

(30) Foreign Application Priority Data
Nov. 27, 2012  (KR) .......................... 10-2012-0135456

(51) Int. Cl.
| | | |
|---|---|---|
| *A61K 47/42* | (2017.01) | |
| *A61K 9/16* | (2006.01) | |
| *A61K 31/136* | (2006.01) | |
| *A61K 31/4745* | (2006.01) | |
| *A61K 31/704* | (2006.01) | |
| *A61K 31/7068* | (2006.01) | |
| *A61K 31/437* | (2006.01) | |
| *A61K 31/727* | (2006.01) | |
| *A61K 31/737* | (2006.01) | |
| *A61K 38/38* | (2006.01) | |
| *A61K 47/36* | (2006.01) | |

(52) U.S. Cl.
CPC ............ *A61K 47/42* (2013.01); *A61K 9/1652* (2013.01); *A61K 9/1658* (2013.01); *A61K 31/136* (2013.01); *A61K 31/437* (2013.01); *A61K 31/4745* (2013.01); *A61K 31/704* (2013.01); *A61K 31/7068* (2013.01); *A61K 31/727* (2013.01); *A61K 31/737* (2013.01); *A61K 38/385* (2013.01); *A61K 47/36* (2013.01)

(58) Field of Classification Search
None
See application file for complete search history.

(56) References Cited

U.S. PATENT DOCUMENTS

| | | |
|---|---|---|
| 4,060,081 A | 11/1977 | Yannas et al. |
| 4,925,677 A | 5/1990 | Feijen |
| 5,041,292 A * | 8/1991 | Feijen .................. A61K 9/1652 424/423 |
| 5,932,248 A | 8/1999 | Chen et al. |
| 6,090,925 A | 7/2000 | Woiszwillo et al. |
| 7,442,385 B2 | 10/2008 | Lewis et al. |
| 2007/0275991 A1 | 11/2007 | Lewis et al. |
| 2015/0265530 A1 | 9/2015 | Xu et al. |
| 2015/0352050 A1 | 12/2015 | Kim et al. |

FOREIGN PATENT DOCUMENTS

| | | |
|---|---|---|
| CN | 1139380 A | 1/1997 |
| EP | 0357401 A2 | 3/1990 |
| EP | 2926806 A1 | 10/2015 |
| JP | S5247912 A | 4/1977 |
| JP | H02-188534 A | 7/1990 |
| JP | H08507806 A | 8/1996 |
| JP | H09-505059 A | 5/1997 |
| JP | 2009-538926 A | 11/2009 |
| JP | 2010-189373 A | 9/2010 |
| JP | 2011-522879 A | 8/2011 |
| JP | 2016-505530 A | 2/2016 |
| KR | 1020030012742 A | 2/2003 |
| KR | 10200500425007 A | 5/2005 |
| KR | 10-1125231 B1 | 3/2012 |
| WO | WO-95/13798 A1 | 5/1995 |
| WO | WO-2009/150651 A1 | 12/2009 |
| WO | WO-2014/077629 A1 | 5/2014 |

OTHER PUBLICATIONS

US 5,849,884, 12/1998, Woiszwillo et al. (withdrawn)
Gewirtz DA. A critical evaluation of the mechanisms of action proposed for the antitumor effects of the anthracycline antibiotics adriamycin and daunorubicin. Biochem Pharmacol. Apr. 1, 1999;57(7):727-41.*

(Continued)

*Primary Examiner* — Marcela M Cordero Garcia
*Assistant Examiner* — Jia-Hai Lee
(74) *Attorney, Agent, or Firm* — Clark & Elbing LLP; Susan M. Michaud

(57) ABSTRACT

The present invention relates to a biodegradable microbead having improved adsorptive power to anticancer drugs, to a method for preparing same, and to a method for treating cancer using same. According to the present invention, a rigid bead having excellent adsorptive power to anticancer drugs can be prepared through cross-linking and an amide bond between an albumin and an anionic polymer. Also, the microbead of the present invention is prepared by a biocompatible and biodegradable polymer so as to be safe when applied to the human body. Further, the microbead of the present invention can effectively inhibit the growth of a tumor by effectively blocking a blood vessel which supplies nutrients to a liver tumor, while continuously releasing anticancer drugs which are adsorbed into the surface of the bead. Thus, the present invention can be usefully applied to a chemoembolization of liver cancer.

10 Claims, 3 Drawing Sheets

(56) References Cited

OTHER PUBLICATIONS

Umesh R. Desai. Heparins. 2000 VCU School of Pharmacy.*
EDC kit instructions. 2011 Thermo Fisher Scientific Inc.*
Taylor et al. Irinotecan drug eluting beads for use in chemoembolization: In vitro and in vivo evaluation of drug release properties. European journal of pharmaceutical sciences. 2007; 30: 7-14.*
Jones et al. Albumin microspheres as vehicles for the sustained and controlled release of doxorubicin. J. Pharm. Pharmacol. 1989, 41: 813-816.*
Richard F. Lee. Agents Which Promote and Stabilize Water-in-Oil Emulsions. Spill Science & Technology Bulletin, vol. 5, No. 2, pp. 117-126, 1999.*
Orienti et al. Progesterone-loaded albumin microparticles. Journal of Controlled Release. 1993; 27: 1-7.*
Fischer MJ. Amine coupling through EDC/NHS: a practical approach. Methods Mol Biol. 2010;627:55-73.*
Cremers et al., "Albumin-heparin microspheres as carriers for cytostatic agents," J Con Rel. 11:167-79 (1990).
Wang et al., "Pingyangmycin loaded bovine serum albumin microspheres for chemoembolization therapy—in vitro and in vivo studies," Int J Pharm. 351(1-2):219-26 (2008).
International Search Report for International Patent Application No. PCT/KR2013/010420, dated Feb. 10, 2014 (7 pages).
"Biodegradable," Oxford Dictionary of Biochemistry and Molecular Biology. Edited by Richard Cammack et al. 2nd ed. 2006 (3 pages).
Artzi et al., "In vivo and in vitro tracking of erosion in biodegradable materials using non-invasive fluorescence imaging," Nat Mater. 10(9):704-9 (2011) (7 pages).
Chen et al., "Synthesis of albumin-dextran sulfate microspheres possessing favourable loading and release characteristics for the anticancer drug doxorubicin," J Con Rel. 31(1):49-54 (1994).
D'Urso et al., "Chapter 4: Bioapplicaton of poly(ethylene glycol)-albumin hydrogens: matrix for enzyme immobilization," American Chemical Society. 25-41 (1996), accessed at <http://pubs.acs.org/doi/abs/10.1021/bk-1996-0627.ch004> on Jul. 8, 2017 (17 pages).
Eubeler, "Biodegradation of synthetic polymers in the aquatic environment," BASF. accessed at https://elib.suub.uni-bremen.de/edocs/00101809-1.pdf on Jul. 8, 2017 (2010) (209 pages).
Extended European Search Report dated Mar. 18, 2016 for European Patent Application No. 13854991.0, Kim et al., "Biodegradable microbeads with improved anticancer drug adsorptivity, containing albumin and dextran sulfate, and preparation method therefor," filed Nov. 15, 2013 (8 pages).
Imamura et al., "Lung cancer treatment and ethnic difference," Nippon Rinsho. 66(6):721-6 (22 pages).
Julinová et al., "Initiating biodegradation of polyvinylpyrrolidone in an aqueous aerobic environment," Proceeding of ECOpole. 6(1):121-7 (2012).
Kwon, Glen Sung Soo, dissertation: "Albumin-heparin microspheres for drug delivery," Doctor of Philosophy, University of Utah, 1991 (241 pages).
Office Action dated Jan. 11, 2017 for Chinese Patent Application No. 201380059670.4, Kim et al., "Biodegradable microbeads with improved anticancer drug adsorptivity, containing albumin and dextran sulfate, and preparation method therefor," filed Nov. 15, 2013 (28 pages).
Office Action dated Jan. 17, 2017 for Japanese Patent Application No. 2015-542954, Kim et al., "Biodegradable microbeads with improved anticancer drug adsorptivity, containing albumin and dextran sulfate, and preparation method therefor," filed Nov. 15, 2013 (7 pages).
Office Action dated May 10, 2016 for Japanese Patent Application No. 2015-542954, Kim et al., "Biodegradable microbeads with improved anticancer drug adsorptivity, containing albumin and dextran sulfate, and preparation method therefor," filed Nov. 15, 2013 (6 pages).
Office Action dated May 5, 2016 for Chinese Patent Application No. 201380059670.4, Kim et al., "Biodegradable microbeads with improved anticancer drug adsorptivity, containing albumin and dextran sulfate, and preparation method therefor," filed Nov. 15, 2013 (28 pages).
Shalaby et al., "Synthesis of enzyme-digestible interpenetrating hydrogel networks by gamma-irradiation,". J Bioactive Compatible Polymers. 8(1):3-23 (1993).
Ulbricht et al., "On the biodegradability of polyethylene glycol, polypeptoids and poly(2-oxazoline)s," Biomaterials. 35(17):4848-61 (2014).
Yapel Jr., Albumin Microspheres: Heat and Chemical Stabilization. *Methods in Enzymology*, vol. 112. Academic Press, Inc., p. 3-18 (1985).
Office Action from Chinese Application No. 201380061708.1, entitled "Biodegradable Microbead Comprising Anionic Polymer for Improving Adsorptive Power to Anticancer Drugs, and Method for Preparing Same," dated Nov. 28, 2017.
Arshady, "Microspheres and microcapsules: a survey of manufacturing techniques. Part 1: suspension cross-linking," Polymer Engineering and Science. 29(24):1746-58 (1989).
Burgess et al., "Potential use of albumin microspheres as a drug delivery system. I. Preparation and in vitro release of steroids," Int J Pharmaceutics. 39(1-2):129-36 (1987).
Cremers et al., "Adriamycin loading and release characteristics of albumin-heparin conjugate microspheres," Journal of Controlled Release. 29:143-55 (1994).
Cremers et al., "Degradation and intrahepatic compatibility of albumin-heparin conjugate microspheres," Biomaterials. 15(8):577-85 (1994).
Cremers et al., "Preparation and characterization of albumin-heparin microspheres," Biomaterials. 15(1):38-48 (1994).
Extended European Search Report dated Oct. 29, 2015, for European Patent Application No. 13858512.0, Kim et al., "Biodegradable microbead comprising anionic polymer for improving adsorptive power to anticancer drugs, and method for preparing same," filed Nov. 15, 2013 (5 pages).
Notice of Allowance for Japanese Patent Application No. 2015-543962, dated Oct. 18, 2016, Kim et al., "Biodegradable Microbead Comprising Anionic Polymer for Improving Adsorptive Power to Anticancer Drugs, and Method for Preparing Same," filed Nov. 15, 2013 (5 pages).
Office Action dated May 27, 2017 for Chinese Application No. 201380061708.1, Kim et al., "Biodegradable Microbead Comprising Anionic Polymer for Improving Adsorptive Power to Anticancer Drugs, and Method for Preparing Same," filed Nov. 15, 2013 (22 pages).
Office Action dated Nov. 23, 2016 for Chinese Application No. 201380061708.1, Kim et al., "Biodegradable Microbead Comprising Anionic Polymer for Improving Adsorptive Power to Anticancer Drugs, and Method for Preparing Same," filed Nov. 15, 2013 (21 pages).
Office Action for Japanese Patent Application No. 2015-543962, dated Mar. 4, 2016, Kim et al., "Biodegradable Microbead Comprising Anionic Polymer for Improving Adsorptive Power to Anticancer Drugs, and Method for Preparing Same," filed Nov. 15, 2013 (9 pages).
Office Action for Japanese Patent Application No. 2016-226549, dated Jul. 25, 2017, Kim et al., "Biodegradable Microbeads Containing Anionic Polymer Having Improved Anti-Cancer Agent Adsorption Capability, and Method for Preparing the Same," filed Nov. 22, 2016 (9 pages).
Office Action for Korean Patent Application No. 10-2013-0139304 dated Mar. 26, 2015, Yoon et al., "Biodegradable Microbeads with an Improved Ability to Absorb Antitumor Agent Comprising Anionic Polymer and Methods of Preparing Thereof," filed Nov. 15, 2013 (7 pages).
Sha, "Development of controlled release carrier and experimental study on functional tissue-engineered skin constructed by the same," Chinese Doctoral Dissertations Full-text Database (Medicine and Health Sciences, 1), dated Jan. 15, 2009 (9 pages).

(56) References Cited

OTHER PUBLICATIONS

Office Action dated Apr. 3, 2018 for Japanese Patent Application No. 2016-226549, Kim et al., "Biodegradable Microbeads Containing Anionic Polymer Having Improved Anti-Cancer Agent Adsorption Capability, and Method for Producing the Same," filed Nov. 22, 2016 (6 pages).

* cited by examiner

BIODEGRADABLE MICROBEAD COMPRISING ANIONIC POLYMER FOR IMPROVING ADSORPTIVE POWER TO ANTICANCER DRUGS, AND METHOD FOR PREPARING SAME

TECHNICAL FIELD

The present invention relates to biodegradable microbeads with improved anticancer drug adsorptivity, and a method for preparing the same, and a method for treating cancer using the same.

BACKGROUND ART

Recent development of imaging technologies can locate cancer that is hiding in the body, and thus the cancer can be removed by several methods such as radiation irritation and endoscopy operation. However, even though the exact location of the cancers is founded, the surgical exclusion of the cancers is impossible due to several reasons, such as the cancer spreading out all over the whole organs or adjoining to another organ. Liver cancer, pancreatic cancer, or the like, even though detected, cannot be radically cured through surgical operation.

Currently, transarterial chemoembolization (TACE), which is most commonly done in the treatment of a liver tumor, is a treatment wherein an anticancer drug is administered to the artery which supplies nutrition to the liver tumor, and then the blood vessel is blocked. Liver tissues receive oxygen and nutrients through the portal vein which turns around the small intestine and large intestine, and the hepatic artery, which comes out directly from the main artery. Normal liver tissues receive blood from mainly the portal vein, and the tumor tissues receive blood from mainly the hepatic artery. Therefore, in cases where an anticancer drug is administered to the hepatic artery, which supplies nutrition to the tumor, and then the blood vein is blocked, only the tumor can be selectively necrotized without harming normal liver tissues. Such a treatment has many advantages, such as having no restrictions according to the progression of cancer and thus having a wide range of applications, and having a few limitations in the objects of the treatment, and thus currently makes a large contribution on the improvement in the cure rate of the liver cancer. As for chemoembolization, a catheter is first inserted into the femoral artery in the groin and approaches the hepatic artery, and then a vascular contrast medium is injected to obtain information necessary for the treatment, such as positions, sizes, and blood supply aspects of tumors. When the treatment protocol is decided, a thin tube with a thickness of about 1 mm is inserted into the catheter, and then the artery to be targeted is found, followed by surgical operation.

Currently, representatively, hepatic embolization using lipiodol has been clinically applied most frequently, and a significant number of patent technologies using the hepatic embolization have also been reported. Lipiodol contains a lot of iodine as a constituent element, and thus allows CT imaging, thereby providing a convenient surgical procedure. However, in order to load doxorubicin, an injection in which a drug is dissolved needs to be shaken and mixed with oily lipiodol immediately before the surgical operation. In addition, it has been clinically reported that after the surgical operation, the doxorubicin dissolved in an aqueous phase does not accumulate in the liver cancer site, but promptly leaks into the body blood, thereby failing to obtain a sufficient anticancer effect and causing a considerable side effect to patients.

U.S. Pat. No. 7,442,385 discloses a method wherein, after polyvinylalcohol (PVA) is cross-linked to prepare micro-sized particles, doxorubicin as a cancer drug is adsorbed on surfaces of beads via an electric attraction and then transferred to the liver cancer site, thereby attaining both a sustained release of anticancer drug and an embolization effect. For achieving this, during a cross-linkage procedure of polyvinylalcohol, 2-acrylamido-2-methylpropane sulfonic acid (AMPS), which is an anionic monomer, is covalently linked to the end of the cross-linkage to modify the polymer, thereby allowing the polymer to adsorb an anionic drug, such as doxorubicin. However, according to the hepatic embolization using polyvinylalcohol, cross-liked PVA does not degrade in the body, and thus, after the necrotization of the liver tumor, PVA beads were irregularly diffused in the body, causing an inflammation, or more unfortunately, the PVA beads go down the blood vessel and spreads into another organ, causing cerebrovascular disease. Therefore, a drug delivery system capable of achieving both a function as an anticancer drug carrier and a vascular embolization function to solve the foregoing problems is required.

Throughout this application, various patents and publications are referenced and citations are provided in parentheses. The disclosure of these patents and publications in their entities are hereby incorporated by references into this application in order to more fully describe this invention and the state of the art to which this invention pertains.

DETAILED DESCRIPTION OF THE INVENTION

Technical Problem

The present inventors have endeavored to develop a method for preparing microbeads, capable of solving the problem in that existing microbeads for the local treatment of cancer do not degrade in the body, allowing large amounts of an anticancer drug to be adsorbed onto microbeads, and simplifying the preparing process to improve economic efficiency. Further, the present inventors have endeavored to prepare stronger microbeads including an anionic polymer. As a result, the present inventors have prepared microbeads in which albumin is cross-linked, by preparing a conjugate in which albumin is amide-bonded to a biocompatible anionic polymer having a sulfonate group, emulsifying the conjugate to form micro-sized bubbles, and cross-linking the micro-sized bubbles, and thus have completed the present invention.

Therefore, an aspect of the present invention is to provide biodegradable microbeads with improved anticancer drug adsorptivity.

Another aspect of the present invention is to provide a method for preparing biodegradable microbeads with improved anticancer drug adsorptivity.

Still another aspect of the present invention is to provide a method for treating cancer by administering the microbeads.

Other objects and advantages of the present invention will become apparent from the detailed description to follow taken in conjunction with the appended claims and drawings.

Technical Solution

In accordance with an aspect of the present invention, there are provided biodegradable microbeads with improved anticancer drug adsorptivity, wherein the biodegradable microbeads comprise an albumin-anionic polymer conjugate in which albumin is amide-bonded to an anionic polymer; wherein the anionic polymer is biocompatible, has a sulfonate group, and has an amine group or a carboxyl group; and wherein the albumin is cross-linked.

The present inventors have endeavored to develop a method for preparing microbeads, capable of solving the problem in that existing microbeads for the local treatment of cancer do not degrade in the body, allowing large amounts of an anticancer drug to be adsorbed onto microbeads, and simplifying the preparing process to improve economic efficiency. Further, the present inventors have endeavored to prepare stronger microbeads including an anionic polymer. As a result, the present inventors have prepared microbeads in which albumin is cross-linked, by preparing a conjugate in which albumin is amide-bonded to a biocompatible anionic polymer having a sulfonate group, emulsifying the conjugate to form micro-sized bubbles, and cross-linking the micro-sized bubbles.

According to one embodiment of the present invention, the microbeads further comprise an anticancer drug adsorbed onto a bead surface by an electrostatic attraction with the anionic polymer.

In a specific embodiment, the anticancer drug is an anthracycline based anticancer drug. Examples of the anthracycline based anticancer drug are doxorubicin, daunorubicin, epirubicin, idarubicin, gemcitabine, mitoxantrone, pararubicin, and valrubicin In another specific embodiment, the anticancer drug is irinotecan.

According to one embodiment of the present invention, the microbeads of the present invention are microbeads for chemoembolization for the treatment of solid cancer.

In one specific embodiment, the microbeads of the present invention are beads for chemoembolization for liver cancer (hepatic artery embolization). As for the solid cancer to which embolization is applicable besides the treatment of liver cancer, rectal cacinom may be treated through rectal artery (K. Tsuchiya, *Urology*. April; 55(4):495-500 (2000)).

The microbeads of the present invention includes, as constituent components, albumin and a biocompatible anionic polymer amide-bonded to the albumin. The albumin is amide-bonded with a carboxyl group or an amine group of the anionic polymer and cross-linked, thereby serving as a support of forming and maintaining a shape of microbeads. The anionic polymer is amide-bonded with the amine group or carboxyl group of the albumin, and serves to allow the anticancer drug to be adsorbed on surfaces of the microbeads. The albumin and anionic polymer, which are both biocompatible polymer materials, can degrade in the body, and thus can solve problems caused by the non-degradation of conventional beads using polyvinylalcohol in the body, for example, polyvinylalcohol is irregularly diffused, causing an inflammation, or goes down the blood vessel and spreads into another organ, causing cerebrovascular disease.

As used herein, the term "biodegradable" refers to being capable of degrading when exposed to a physiological solution, and for example, refers to being capable of degrading by the body fluid or microorganisms in the living bodies of mammals including a human being.

According to an embodiment of the present invention, the albumin is a protein which is widely distributed in the body fluid, and includes animal albumins and vegetable albumins.

In one specific embodiment, the animal albumins include ovalbumin, serum albumin, lactalbumin, and miogen, and the vegetable albumins include leucosin (barely seeds), legumelin (peas), and lysine (castor seeds). The albumin includes albumin variants.

According to an embodiment of the present invention, the biocompatible anionic polymer includes a glycosaminoglycan based polymer.

In one specific embodiment, the glycosaminoglycan based polymer is selected from the group consisting of chondroitin sulfate, dermatan sulfate, heparan sulfate, heparin, keratan sulfate, and hyaluronan.

According to one embodiment of the present invention, the cross-linkage of the albumin is performed by thermal cross-linkage.

According to another embodiment of the present invention, the cross-linkage of albumin is performed by an aldehyde cross-linking agent. In one specific embodiment, the aldehyde based cross-linking agent is selected from the group consisting of glutaraldehyde, formaldehyde, dialdehyde starch, succinate aldehyde, acryl aldehyde, oxalaldehyde, 2-methylacrylaldehyde, and 2-oxopropanal.

According to one embodiment of the present invention, the anticancer drug adsorptivity of the microbeads of the present invention is 10-100 mg per 1 ml of microbeads. The anticancer drug adsorptivity of the microbeads of the present invention is 20-60 mg per 1 ml of microbeads for one specific embodiment, 20-55 mg per 1 ml of microbeads for another specific embodiment, and 20-50 mg per 1 ml of microbeads for still another specific embodiment.

The microbeads of the present invention may be packaged in a vial together with a solution (wet microbead type), and selectively pulverized for the use (dry microbead type).

In accordance with another aspect of the present invention, there is provided a method for preparing biodegradable microbeads with improved anticancer drug adsorptivity, the method including:

(a) obtaining an albumin-anionic polymer conjugate by allowing albumin to amide-bond to an anionic polymer, the anionic polymer (i) being biodegradable, (ii) having a sulfonate group, and (iii) having an amine group or a carboxyl group;

(b) emulsifying the albumin-anionic polymer conjugate in step (a) to form micro-sized bubbles; and (c) cross-linking the micro-sized bubbles in step (b) to form microbeads in which albumin is cross-linked.

According to an embodiment of the present invention, the method of the present invention further includes, after step (c), (d) bringing the microbeads in step (c) into contact with an anticancer drug to allow the anticancer drug to be adsorbed onto surfaces of the microbeads by an electrostatic attraction with the anionic polymer of the microbeads.

According to one embodiment of the present invention, the composition ratio of the albumin and the anionic polymer in step (a) may be 10-25:10-10% (W/V) based on a solution containing the two components (a solution for preparing beads). In cases where the amount of the albumin is remarkably smaller than that of the anionic polymer in the solution for preparing beads, the beads are not strongly formed. In cases where the amount of the anionic polymer is remarkably smaller than that of the albumin, the anticancer drug adsorptivity deteriorates. According to the present invention, the beads are strongly formed through amid bonding between the albumin and the anionic polymer, and thus the amount of the anionic polymer can be used in an amount equal or similar to that of the albumin when the beads are prepared, and as a result, the anticancer drug adsorptivity can be increased.

The composition ratio of the albumin and the anionic polymer is 12-25:15-10% (W/V) for one specific embodiment, 12-23:15-10% (W/V) for another specific embodiment, 15-23:15-10% (W/V) for still another specific embodiment, and 15-20:15-10% (W/V) for still another specific embodiment.

According to an embodiment of the present invention, the emulsification of the albumin-anionic polymer conjugate in step (b) is performed using an organic solvent containing natural oil or a viscosity increasing agent.

Examples of usable natural oil may be MCT oil, cottonseed oil, corn oil, almond oil, apricot oil, avocado oil, babassu oil, chamomile oil, canola oil, cocoa butter oil, coconut oil, cod-liver oil, coffee oil, fish oil, flax seed oil, jojoba oil, gourd oil, grape seed oil, hazelnut oil, lavender oil, lemon oil, mango seed oil, orange oil, olive oil, mink oil, palm tree oil, rosemary oil, sesame oil, shea butter oil, bean oil, sunflower oil, walnut oil, and the like.

Examples of the usable organic solvent may be acetone, ethanol, butyl acetate, and the like. The organic solvent may include a viscosity-increasing agent for providing appropriate viscosity. Examples of the viscosity-increasing agent may be cellulose based polymers, such as hydroxymethyl cellulose, hydroxypropyl methyl cellulose, and cellulose acetate butyrate.

According to one embodiment of the present invention, the micro-sized bubbles in step (b) may be formed using a microfluidic system or an encapsulator. The microfluidic system is a method wherein beads are prepared using a micro-structured chip. After a smaller tube is positioned inside a larger tube, an aqueous phase and an oil phase are allowed to flow through the tubes in opposite directions, thereby forming beads by tension thereof. That is, when the solution for preparing beads (solution containing albumin-anionic polymer conjugate) as an inner fluid and the natural oil or organic solvent (collection solution) as an outer fluid are allowed to flow, the beads are formed by tension. The beads are collected into the collection solution, and then the beads may be prepared through a cross-linkage reaction.

The encapsulation is similar to electrospinning, and is characterized in that an electric field, which is formed between a nozzle and a collection solution, finely splits water drops generated by tension, thereby dispersing very small-sized droplets. The solution for preparing beads is transferred into a syringe corresponding to the volume thereof, and the syringe is mounted on a syringe pump, and then connected with an encapsulator. In addition, the collection solution is transferred into a dish corresponding to the volume thereof, and then positioned on a stirrer. The environment of the encapsulator is appropriately set, and then the solution for preparing beads is sprayed to the collection solution to form bubbles. Preferably, the conditions of the encapsulator are preferably a flow rate of 1-5 ml/min, applied electric power of 1,000-3,000 V, ultrasonic wave of 2,000-6,000 Hz, and a revolution number of 100 rpm. The size of a release nozzle is selected according to the size of beads to be prepared.

According to another embodiment of the present invention, the micro-sized bubbles in step (b) may be prepared by an emulsifying method wherein a solution for preparing beads is mixed with a collection solution, and then the mixture is stirred at a proper revolution number. Here, the size of the beads depends on the revolution number and the stirring time. When appropriate-sized bubbles are formed, the bubbles are cross-linkaged to form microbeads.

According to an embodiment of the present invention, the stirring continues to maintain a cross-linkage reaction of albumin until the cross-linkage reaction of albumin is completed, and upon completion of the reaction, the beads are washed several times using a large amount of acetone or ethanol for the washing of the collection solution.

In step (c) of the present invention, the micro-sized bubbles obtained in step (b) are cross-linked to prepare microbeads in which albumin is cross-linked.

According to an embodiment of the present invention, the cross-linkage is performed using an aldehyde-based cross-linking agent or by thermal cross-linkage. In cases where the microbeads of the present invention are prepared by thermal cross-linkage, the microbeads have excellent body compatibility due to the non-use of a chemical cross-linkage harmful to the human body, and have economic advantages due to the omission of a removing step of the cross-linking agent.

According to one embodiment of the present invention, the temperature of thermal cross-linkage is 60° C. or higher, and the time for thermal cross-linkage is 1 to 4 hours. In one specific embodiment, the temperature for thermal cross-linkage is 60-160° C.

In accordance with still another aspect of the present invention, there is provided a method for treating cancer, the method including administering to a patient biodegradable microbeads with improved anticancer drug adsorptivity, wherein the microbeads includes an albumin-anionic polymer conjugate in which albumin is amide-bonded to an anionic polymer, and an anticancer drug adsorbed on surface thereof by an electrostatic attraction with the anionic polymer; the anionic polymer is biocompatible, has a sulfonate group, and has an amine group or a carboxyl group; and the albumin is cross-linked.

According to the present invention, the microbeads of the present invention are administered into a cancer patient, thereby treating cancer through chemoembolization.

According to one embodiment of the present invention, the patient is a liver cancer patient, and the microbeads are administered to the hepatic artery of the patient.

Advantageous Effects

The features and advantages of this invention will be summarized as follows:

(i) The present invention provides biodegradable microbeads with improved anticancer drug adsorptivity, and a method for preparing the same, and a method for treating cancer using the same.

(ii) The present invention can provide strong beads having excellent anticancer drug adsorptivity due to the amide bonding between the albumin and the anionic polymer and the cross-linkage.

(iii) The microbeads of the present invention are safe to the human body since the microbeads are prepared as a biocompatible and biodegradable polymer, and can effectively inhibit the growth of tumors by effectively blocking the blood vessel which supplies nutrition to the liver tumor and continuously releases an anticancer drug adsorbed onto the surfaces of the beads.

(iv) Therefore, the present invention can be favorably utilized for chemoembolization for liver cancer.

MODE FOR CARRYING OUT THE INVENTION

Figure 1:
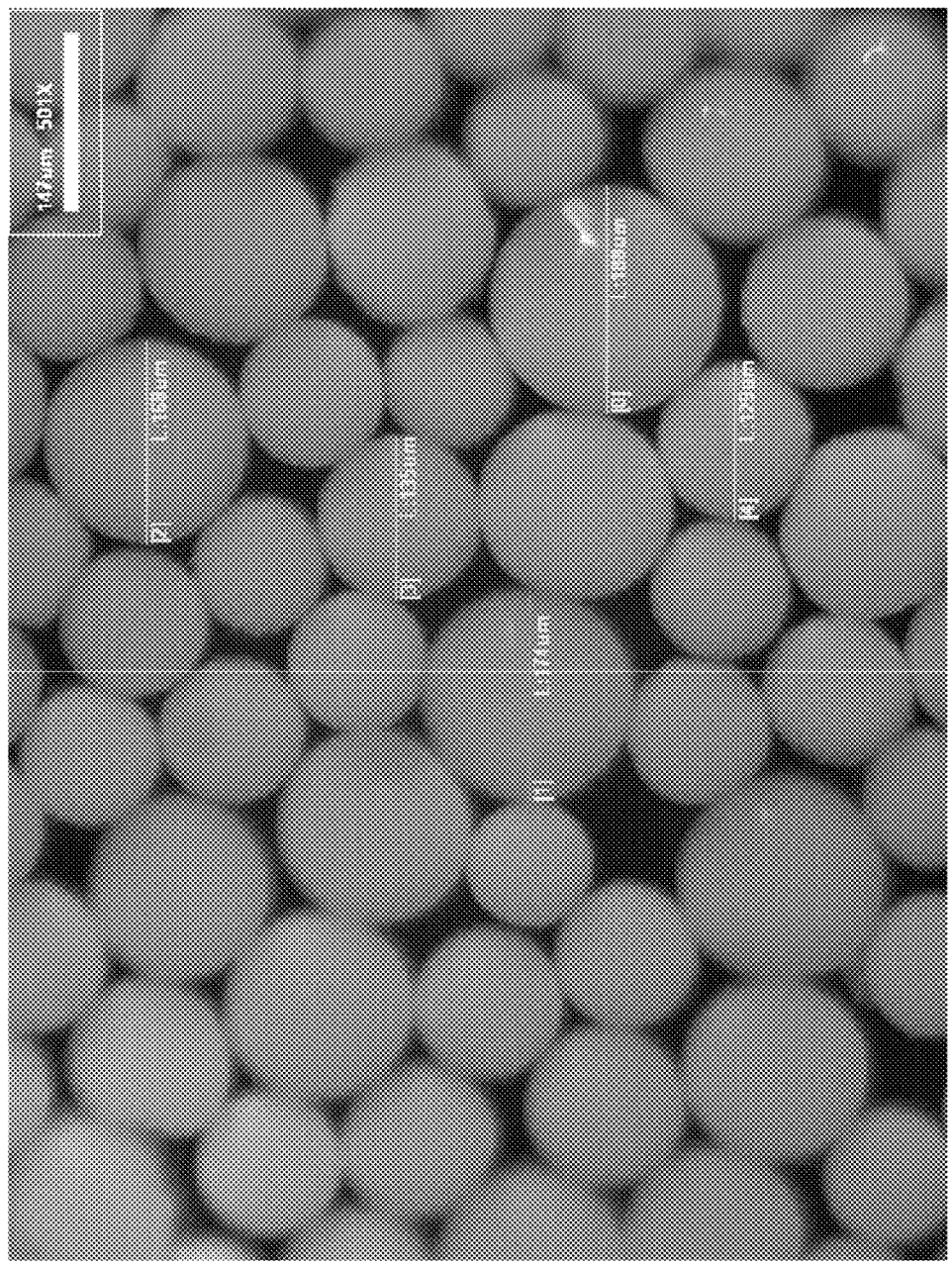
FIG. 1 shows microbeads prepared by the present invention.
Figure 2:
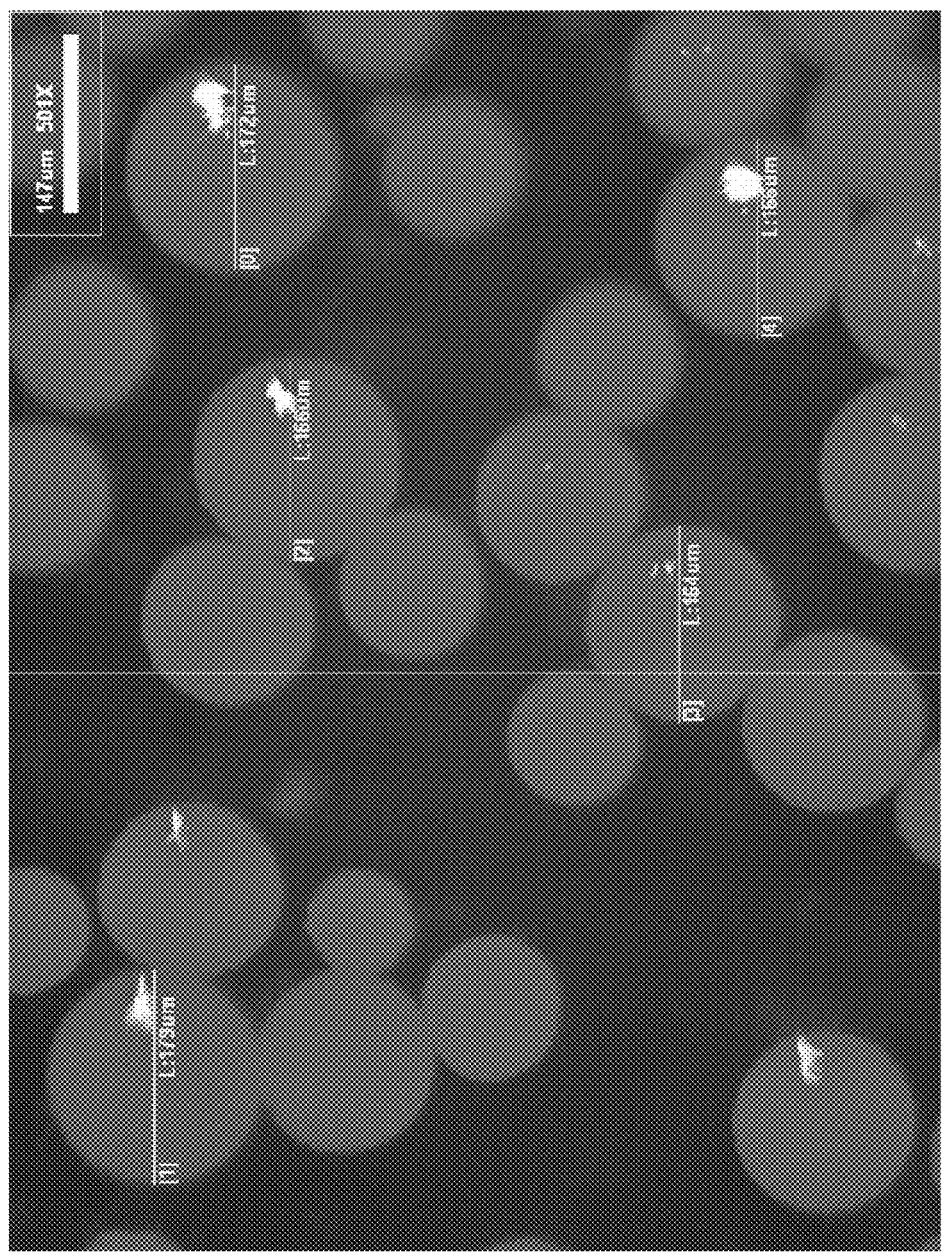
FIG. 2 shows doxorubicin-adsorbed microbeads prepared by the present invention.

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1. Preparation of Microbeads for Chemoembolization

In order to amide-bond an amine group ($NH_2$—) of albumin and a carboxyl group (COOH—) of chondroitin sulfate, sodium cyanoborohydride (SCBH) or 1-ethyl-3-(3-dimethylamino-propyl)carbodiimide (EDS)/N-hydroxy succinimide (NHS) was used. First, the anionic polymer was activated using SCBH or EDC/NHS, and then reaction-bonded to albumin having compositions 1-5 of table 1 below. After that, the resultant material was dialyzed for 1-2 days to remove unreacted materials, thereby obtaining a solution for preparing beads.

TABLE 1

Composition of solution for preparing beads

| | W/V % | COMPOSITION 1 | COMPOSITION 2 | COMPOSITION 3 | COMPOSITION 4 | COMPOSITION 5 |
|---|---|---|---|---|---|---|
| Albumin | Human serum albumin | 15 | 20 | | | 10 |
| | Bovine serum albumin | | | 15 | 20 | 10 |
| Anionic polymer | Chondroitin sulfate | 15 | 10 | 15 | 10 | 10 |
| | Dermatan sulfate | 15 | 10 | 15 | 10 | 10 |
| | Heparan sulfate | 15 | 10 | 15 | 10 | 10 |
| | Heparin | 15 | 10 | 15 | 10 | 10 |

Microparticles were prepared using an encapsulator. The preparation conditions were: a flow rate of 3 ml/min, applied electric power of 1,000 V, ultrasonic wave of 3,000 Hz, and a revolution number of 100 rpm. The size of a release nozzle was selected according to the size of beads to be prepared. The solution for preparing beads was transferred into a syringe corresponding to the volume thereof, and the syringe is mounted on a syringe pump. After that, the syringe is connected with an encapsulator (B-390, BUCHI), and the collection solution was transferred into a dish corresponding to the volume thereof, and then placed on a stirrer. After the environment of the encapsulator was established, the solution for preparing beads was sprayed in the collection solution, and then the collection solution was heated to 120° C. to be cross-linked, thereby forming beads. The time for cross-linkage was 2 hours, and n-butyl acetate in which 10% cellulose acetate butylate was dissolved was used as the collection solution.

In addition, for chemical cross-linkage, the solution for preparing beads was sprayed in the collection solution, followed by cross-linkage using an aldehyde-based cross-linking agent, such as glutaraldehyde or formaldehyde, for 24 hours.

Example 2. Doxorubicin Adsorption Test

The doxorubicin adsorption test was conducted as follows. First, 50 mg of doxorubicin was dissolved in 2 ml of distilled water. Then, 1 ml of beads were taken, and put in a doxorubicin solution, followed by mixing well. After the mixture was left at room temperature for 20 minutes, the supernatant was taken, and then the absorbance at 483 nm was measured by an ultraviolet spectrometer. The amount of doxorubicin leaking out from 50 mg/2 ml of the doxorubicin solution may be determined by calculating the concentration through the comparison with the previously prepared calibration curve, and such a value was the amount of doxorubicin adsorbed on the beads. The test results are shown in table 2.

TABLE 2

| Classification | Composition | Chondroitin sulfate | Dermatan sulfate | Heparan sulfate | Heparin |
|---|---|---|---|---|---|
| Thermal cross-linkage | 15:15 | 47 ± 2 mg/ml | 42 ± 1 mg/ml | 45 ± 3 mg/ml | 42 ± 2 mg/ml |
| | 20:10 | 42 ± 3 mg/ml | 38 ± 2 mg/ml | 40 ± 1 mg/ml | 36 ± 3 mg/ml |
| Aldehyde based cross-linking agent | 15:15 | 36 ± 3 mg/ml | 33 ± 2 mg/ml | 34 ± 3 mg/ml | 32 ± 2 mg/ml |
| | 20:10 | 30 ± 2 mg/ml | 28 ± 1 mg/ml | 29 ± 2 mg/ml | 26 ± 3 mg/ml |

As shown in table 2, it was verified that, as a result of using various glycosaminoglycan based anionic polymers, the doxorubicin adsorption amount exhibited similar aspects and were proportional to the content of the anionic polymer.

In the same manner, as a result of measuring daunorubicin and epirubicin adsorption amounts, the daunorubicin and epirubicin adsorption amounts were verified to be equivalent to the doxorubicin adsorption amount (table 3).

TABLE 3

| Classification | Classification | Composition | Chondroitin sulfate | Dermatan sulfate | Heparan sulfate | Heparin |
|---|---|---|---|---|---|---|
| Doxorubicin | Thermal cross-linkage | 15:15 | 47 ± 2 mg/ml | 42 ± 1 mg/ml | 45 ± 3 mg/ml | 42 ± 2 mg/ml |
| | | 20:10 | 42 ± 3 mg/ml | 38 ± 2 mg/ml | 40 ± 1 mg/ml | 36 ± 3 mg/ml |
| | Cross-linking agent | 15:15 | 36 ± 3 mg/ml | 33 ± 2 mg/ml | 34 ± 3 mg/ml | 32 ± 2 mg/ml |
| | | 20:10 | 30 ± 2 mg/ml | 28 ± 1 mg/ml | 29 ± 2 mg/ml | 26 ± 3 mg/ml |
| Daunorubicin | Thermal cross-linkage | 15:15 | 46 ± 3 mg/ml | 44 ± 2 mg/ml | 44 ± 2 mg/ml | 42 ± 2 mg/ml |
| | | 20:10 | 43 ± 2 mg/ml | 38 ± 3 mg/ml | 41 ± 1 mg/ml | 35 ± 2 mg/ml |
| | Cross-linking agent | 15:15 | 36 ± 3 mg/ml | 33 ± 2 mg/ml | 34 ± 3 mg/ml | 33 ± 1 mg/ml |
| | | 20:10 | 29 ± 3 mg/ml | 28 ± 2 mg/ml | 31 ± 1 mg/ml | 25 ± 3 mg/ml |
| Epirubicin | Thermal cross-linkage | 15:15 | 46 ± 1 mg/ml | 42 ± 2 mg/ml | 44 ± 2 mg/ml | 41 ± 3 mg/ml |
| | | 20:10 | 41 ± 3 mg/ml | 39 ± 1 mg/ml | 41 ± 1 mg/ml | 37 ± 2 mg/ml |
| | Cross-linking agent | 15:15 | 35 ± 2 mg/ml | 35 ± 2 mg/ml | 34 ± 3 mg/ml | 32 ± 2 mg/ml |
| | | 20:10 | 30 ± 2 mg/ml | 28 ± 1 mg/ml | 29 ± 2 mg/ml | 24 ± 3 mg/ml |

Example 3. Doxorubicin Release Test

Figure 3:
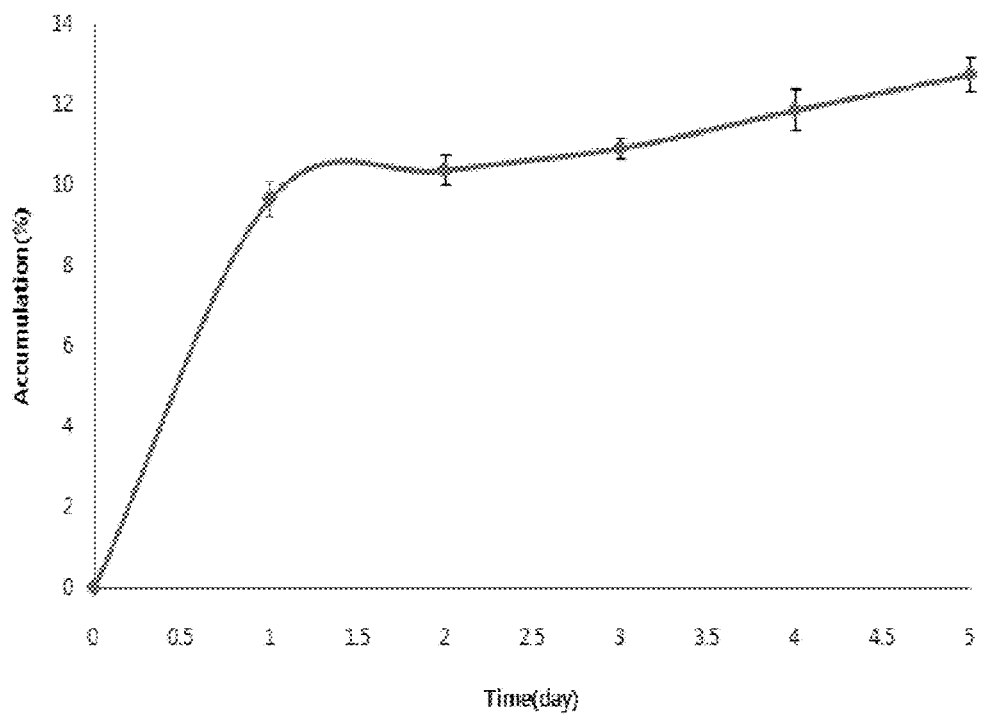
FIG. 3 shows a release behavior of doxorubicin-adsorbed albumin/chondroitin sulfate beads.

In order to verify the drug release behavior, the release test was conducted. The test method was as follows. Beads corresponding to 4.0 mg of doxorubicin were put in a 50-ml conical tube, which was filled with 50 ml of a release solution (PBS, pH 7.4), followed by incubation at 37° C. The release solution was all collected at the time of collection, and then exchanged with a new release solution. The release curve was calculated as an accumulative value. The released drug was assayed by HPLC, and the release results are shown in FIG. 3.

Having described a preferred embodiment of the present invention, it is to be understood that variants and modifications thereof falling within the spirit of the invention may become apparent to those skilled in this art, and the scope of this invention is to be determined by appended claims and their equivalents.

The invention claimed is:

1. Biodegradable microbeads with anticancer drug adsorptivity,
wherein the biodegradable microbeads comprise an albumin-anionic polymer conjugate in which albumin is amide-bonded to an anionic polymer and subsequently is cross-linked by thermal cross-linkage at a temperature 60° C. or higher, and an anticancer drug adsorbed on surfaces of the biodegradable microbead by an electrostatic attraction with the anionic polymer;
wherein the anionic polymer is selected from the group consisting of chondroitin sulfate, dermatan sulfate, keratan sulfate, and hyaluronan.

2. The microbeads of claim 1, wherein the anticancer drug is an anthracycline based anticancer drug.

3. The microbeads of claim 2, wherein the anthracycline based anticancer drug is selected from the group consisting of daunorubicin, doxorubicin, epirubicin, idarubicin, gemcitabine, mitoxantrone, pirarubicin, and valrubicin.

4. The microbeads of claim 1, wherein the anticancer drug is irinotecan.

5. The microbeads of claim 1, wherein the microbeads are microbeads for chemoembolization.

6. The microbeads of claim 5, wherein the chemoembolization is chemoembolization for liver cancer.

7. A method for preparing biodegradable microbeads with anticancer drug adsorptivity, the method comprising:
(a) contacting a mixture of albumin and an anionic polymer with a crosslinking agent and allowing the albumin to amide-bond to the anionic polymer to obtain an albumin-anionic polymer conjugate, wherein the anionic polymer is selected from the group consisting of chondroitin sulfate, dermatan sulfate, heparan sulfate, heparin, keratan sulfate and hyaluronan;
(b) emulsifying the albumin-anionic polymer conjugate in step (a) to form micro-sized bubbles; and
(c) thermally cross-linking the micro-sized bubbles in step (b) to form microbeads in which albumin is cross-linked by thermal cross-linkage at a temperature 60° C. or higher.

8. The method of claim 7, the crosslinking agent is sodium cyanoborohydride (SCBH) or 1-ethyl-3-(3-dimethylaminopropyl)carbodiimide (EDS)/N-hydroxy succinimide (NHS).

9. A method for treating cancer, the method comprising administering to a patient biodegradable microbeads with anticancer drug adsorptivity, wherein the microbeads include an albumin-anionic polymer conjugate in which albumin is amide-bonded to an anionic polymer, and an anticancer drug adsorbed on surface thereof by an electrostatic attraction with the anionic polymer; the anionic polymer is selected from the group consisting of chondroitin sulfate, dermatan sulfate, keratan sulfate and hyaluronan; and the albumin is cross-linked by thermal cross-linkage.

10. The method of claim 9, wherein the patient is a liver cancer patient and the microbeads are administered to the hepatic artery of the patient.

* * * * *